US008815842B2

(12) United States Patent
Furuta

(10) Patent No.: US 8,815,842 B2
(45) Date of Patent: Aug. 26, 2014

(54) ANTI-FOOT-AND-MOUTH DISEASE VIRUS AGENT FOR ANIMAL BELONGING TO FAMILY SUIDAE OR SHEEP, AND METHOD FOR PREVENTION OR TREATMENT OF FOOT-AND-MOUTH DISEASE IN ANIMAL BELONGING TO FAMILY SUIDAE OR SHEEP

(75) Inventor: Yousuke Furuta, Shinjuku-ku (JP)

(73) Assignee: Toyama Chemical Co., Ltd., Tokyo (JP)

( * ) Notice: Subject to any disclaimer, the term of this patent is extended or adjusted under 35 U.S.C. 154(b) by 577 days.

(21) Appl. No.: 12/302,839

(22) PCT Filed: May 29, 2007

(86) PCT No.: PCT/JP2007/060851

§ 371 (c)(1),
(2), (4) Date: Nov. 28, 2008

(87) PCT Pub. No.: WO2007/139081

PCT Pub. Date: Dec. 6, 2007

(65) Prior Publication Data

US 2009/0156580 A1 Jun. 18, 2009

(30) Foreign Application Priority Data

May 31, 2006 (JP) ................................ 2006-151903
Sep. 13, 2006 (JP) ................................ 2006-247698

(51) Int. Cl.

*A61K 31/55* (2006.01)
*A61K 31/4965* (2006.01)
*A23K 1/18* (2006.01)
*C07D 241/24* (2006.01)
*A23K 1/16* (2006.01)

(52) U.S. Cl.

CPC ........... *A23K 1/1625* (2013.01); *A61K 31/4965* (2013.01); *A23K 1/1813* (2013.01); *C07D 241/24* (2013.01); *A23K 1/184* (2013.01); *A23K 1/1609* (2013.01)
USPC ........................................................ 514/215

(58) Field of Classification Search

CPC . A23K 1/1609; A23K 1/1625; A23K 1/1813; A23K 1/184; A23K 31/4965; C07D 241/24
USPC ........................................................ 514/215
See application file for complete search history.

(56) References Cited

U.S. PATENT DOCUMENTS

| | | | | |
|---|---|---|---|---|
| 2,927,027 | A * | 3/1960 | Bousquet et al. | 514/473 |
| 4,748,163 | A | 5/1988 | Schmidt et al. | |
| 5,106,616 | A * | 4/1992 | McAnalley et al. | 424/85.2 |
| 6,787,544 | B2 | 9/2004 | Furuta et al. | |
| 6,800,629 | B2 * | 10/2004 | Egawa et al. | 514/255.05 |
| 2002/0013316 | A1 * | 1/2002 | Furuta et al. | 514/241 |
| 2003/0026842 | A1 * | 2/2003 | Prestrelski et al. | 424/489 |
| 2003/0130213 | A1 | 7/2003 | Egawa et al. | |

FOREIGN PATENT DOCUMENTS

| | | |
|---|---|---|
| EP | 1 112 743 A1 | 7/2001 |
| JP | 41 759 | 1/1966 |
| JP | 61 207388 | 9/1986 |
| JP | 2000 7564 | 1/2000 |
| RU | 2 223 659 C2 | 9/2003 |
| WO | 00 10569 | 3/2000 |

OTHER PUBLICATIONS

Alexander N. Lukashev, Role of recombination in evolution of enteroviruses, 2005, Rev. Med. Virol, 15: 157-167.*
Nonia Pariente et al., "Action of Mutagenic Agents and Antiviral Inhibitors on Foot-and-Mouth Disease Virus", Virus Research, vol. 107, No. 2, Feb. 1, 2005, XP004710642, pp. 183-193.
Office Action issued Dec. 14, 2010, in Russia Patent Application No. 2008152376 (with English-language Translation).

* cited by examiner

*Primary Examiner* — Melenie McCormick
*Assistant Examiner* — Angela Brown-Pettigrew
(74) *Attorney, Agent, or Firm* — Oblon, Spivak, McClelland, Maier & Neustadt, L.L.P.

(57) ABSTRACT

Disclosed is an anti-foot-and-mouth disease virus agent for an animal belonging to the Family Suidae, which comprises 3-oxo-3,4-dihyro-2-pyrazincarboxamide or a salt thereof. The agent is extremely useful for the prevention or treatment of food-and-mouth disease in an animal belonging to the Family Suidae. Also disclosed is an anti-foot-and-mouth disease virus agent for sheep, which comprises 3-oxo-3,4-dihyro-2-pyrazincarboxamide or a salt thereof. The agent is extremely useful for the prevention, therapy or the like of food-and-mouth disease in sheep.

14 Claims, No Drawings

ANTI-FOOT-AND-MOUTH DISEASE VIRUS AGENT FOR ANIMAL BELONGING TO FAMILY SUIDAE OR SHEEP, AND METHOD FOR PREVENTION OR TREATMENT OF FOOT-AND-MOUTH DISEASE IN ANIMAL BELONGING TO FAMILY SUIDAE OR SHEEP

TECHNICAL FIELD

The present invention relates to an anti-foot-and-mouth disease virus agent for an animal belonging to Family Suidae or a sheep (hereinafter referred to as "Suidae animals, etc."), containing 3-oxo-3,4-dihydro-2-pyrazinecarboxamide (hereinafter referred to as T-1105), or a salt thereof; an animal feed for Suidae animals, etc., containing T-1105 or a salt thereof; and a treatment method including a preventive and therapeutic method for foot-and-mouth disease of the Suidae animals, etc.

BACKGROUND ART

Foot-and-mouth disease is one of the strong communicable diseases among domestic animals, that is, artiodactyl animals including a bovine, a pig and a sheep, etc. Further, this disease causes disorders of development, movement and the like in domestic animals, to rapidly drop their commercial value, and is an infectious disease specific to domestic animals but non-infectious to human. For livestock business in the world, foot-and-mouth disease is positioned as the most important animal disease to be alerted from both of the exporting and importing countries' points of view.

Foot-and-mouth disease is also an international infectious disease and is currently prevalent throughout the world including Asia, Africa, and South America. Also in Japan, its outbreak occurred in 2000. Once the disease occurs, many difficulties are accompanied in preventing its propagation because the virus is highly transmissible. The emergence of the disease deals a great blow to the livestock business. Therefore, much effort is expended on the treatment including the prevention and therapy of foot-and-mouth disease worldwide.

The countermeasures to control this disease are strict import restriction, hygiene control, quarantine, and slaughter of affected animals. At an outbreak, a vaccination program is conducted using an inactivated vaccine as a preventive countermeasure in the national or regional level, or in the surroundings of the outbreak area. However, it is difficult to early detect this disease, and the disease spreads so rapidly that the vaccination cannot catch up with it. Furthermore, since the virus is highly mutative, vaccination alone cannot prevent the infection completely. That is, at the present, there is no excellent therapeutic method for the Suidae animals, etc., of Artiodactyla.

WO 00/10569 pamphlet describes that T-1105 has an excellent anti-influenza virus effect (Patent Document 1). It discloses specifically, however, neither an anti-foot-and-mouth disease virus agent for the Suidae animals, etc., nor a treatment method including a preventive or therapeutic method for foot-and-mouth disease of Suidae animals, etc.

Patent Document 1: WO 00/10569 pamphlet

DISCLOSURE OF THE INVENTION

There has been a strong need for an excellent anti-foot-and-mouth disease virus agent for the Suidae animals, etc., and a treatment method including preventive or therapeutic method for foot-and-mouth disease of Suidae animals, etc.

Under these circumstances, the present inventor, as a result of keen examination, has found that an anti-foot-and-mouth disease virus agent containing T-1105 or a salt thereof has a potent foot-and-mouth disease therapeutic effect in a Suidae animal, and is useful for the treatment including therapy of foot-and-mouth disease of the Suidae animal; and thus has completed the invention.

Furthermore, the present inventor has found that the anti-foot-and-mouth disease virus agent containing T-1105 or a salt thereof has a strong foot-and-mouth therapeutic effect in a sheep, and is useful for the treatment including therapy of foot-and-mouth disease of the sheep; and thus has completed the invention.

The anti-foot-and-mouth disease virus agent containing T-1105 or a salt thereof is useful for the treatment including the prevention and therapy of foot-and-mouth disease of the Suidae animals, etc.

BEST MODE FOR CARRYING OUT THE INVENTION

Hereinafter, the present invention will be illustrated in detail.

In this specification, unless otherwise indicated, when a solvate and a hydrate of T-1105 or a salt thereof exists, they can be used. Also various forms of crystals can be used.

A salt of T-1105 includes a usually known salt formed at a hydroxyl group. The salt formed at a hydroxyl group includes, for example, a salt with an alkali metal, such as sodium and potassium; a salt with an alkaline earth metal, such as calcium and magnesium; an ammonium salt; as well as a salt with a nitrogen-containing organic base, such as trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-β-phenethylamine, 1-ephenamine and N,N'-dibenzylethylenediamine. Among these salts described above, a preferable salt includes a pharmacologically acceptable salt, and a sodium salt is more preferable.

The anti-foot-and-mouth disease virus agent for Suidae animals, etc., containing T-1105 or a salt thereof of the invention shows an excellent anti-viral effect on the foot-and-mouth disease virus which belongs to genus *Aphthovirus*. The foot-and-mouth disease virus includes, for example, serotypes A, O and C of European-type, serotype Asia 1 of Asian-type, serotypes SAT1, SAT2 and SAT3 of African-type, and subtypes thereof.

The anti-foot-and-mouth disease virus agent for the Suidae animals, etc., containing T-1105 or a salt thereof of the invention is more effective, in particular for serotypes A, O and C, as well as Asia 1 whose emergence has been observed in Asia.

The Suidae animal in the present invention means an animal which belongs to Family Suidae, Artiodactyla, Mammalia, Vertebrata; specifically includes a pig and a wild boar and is preferably a pig.

T-1105 or a salt thereof may be administered to the Suidae animals, etc., parenterally as injections after diluted with distilled water for injection or physiological saline; or may be administered orally or parenterally as an animal formulation, for example, tablets, large-sized pills, powders, granules, finely divided granules, capsules, emulsions, liquids, suspensions, pre-mixed formulations, syrups, pastes, or aerosols, according to a known pharmaceutical manufacturing method, using pharmaceutically acceptable diluents and excipients as desired.

T-1105 or a salt thereof or the animal formulation thereof can be used as mixed with the animal feed as needed, for example, coarse feeds, such as hay, straw, herbage, green feed soiling crops, root crops and fruits, wild plants, tree leaves, and silage; and concentrate feeds, such as grains, cereals, and mixed fertilizer. Also, it can be used by adding to drinking water and the like.

The preferred form of administration includes administration as injections, such as intramuscular, subcutaneous, and intraperitoneal injections, and mixed-feed oral administration by mixing T-1105 into an animal feed.

The anti-foot-and-mouth disease virus agent for Suidae animals, etc., and the animal feed for Suidae animals, etc., of the present invention can be manufactured, for example, by stabilizing T-1105 or a salt thereof through dilution or encapsulation with solid or liquid carriers to make up, for example, tablets, large-sized pills, powders, granules, finely divided granules, capsules, emulsions, liquids, suspensions, premixed formulations, syrups, pastes, or aerosols, alternatively by dispersing it directly into the feeds or drinks, or carriers and adding it. The solid carriers include, for example, lactose, sucrose, starch, flour, corn flour, bran, soybean oil cake, defatted rice bran, rape cake, bean curd refuse, cellulose, yeast cell, fish meal, peanuts marc, shell meal, and calcium carbonate; the liquid carriers include, for example, water, physiological saline, and physiologically innocuous organic solvents. Also, adjuvants, such as emulsifying agents, dispersing agents, suspending agents, wetting agents, thickening agents, gelling agents, and solubilizing agents can be added as needed. It may take premixed form. Further, preservatives, bacteriocides, vermicides, antioxidants, coloring agents, flavors, antibacterial agents, antibiotics, enzyme preparations, lactobacillus preparations, antipyretics, analgesic agents and anti-inflammatory agents may be compounded. Other animal drugs may be compounded. Also, various kinds of vitamins, minerals, and amino acids may be compounded.

The anti-foot-and-mouth disease virus agent for the Suidae animals, etc., of the present invention is administered for the purpose of treatment including prevention and/or therapy of foot-and-mouth disease to livestock or animals of the Suidae animals, etc. Preferably, it is administered in particular to a pig.

The dosage may be selected appropriately depending on the age, body weight, symptoms of the subject animal and the administration route. For example, a dosage of 1 to 2000 mg/kg of the body weight of an animal may be administered by dividing it into one to several times daily. The frequency can be increased depending on the symptoms. The administration period is not particularly limited, while usually 1 to 10 days of administration is enough to obtain sufficient efficacy. Also it can be administered intermittently.

EXAMPLES

Now, the present invention will be illustrated by Test Examples, which in no way limit the present invention. T-1105 or a salt thereof of the present invention can be obtained by purchasing a commercial product or can be produced by any known method or methods based thereon or combinations thereof. The following experiments in Test Example 1 to 3 were conducted at National Institute of Animal Health in Tokyo of National Agriculture and Food Research Organization, the independent administrative institution.

Test Example 1

In Vitro Anti-Foot-and-Mouth Disease Virus Effect (1) The effect of T-1105 on the anti-foot-and-mouth disease virus (O/JPN/2000 strain) was determined.

The foot-and-mouth disease virus (O/JPN/2000 strain) was adsorbed onto swine derived kidney subcultured cells at approximately 30 to 100 copies/dish at 37° C. for 1 hour. The virus solution was removed and the cells were washed with MEM culture medium which had been adjusted to pH 7.4, followed by overlaying 2% bovine serum containing MEM culture medium supplemented with 1.5% methylcellulose in which 20 µg/mL of T-1105 was diluted by 2 steps and added. After 3 days of cultivation, cells were fixed and stained with 10% neutral buffered formalin containing 0.2% crystal violet, and then the number of plaques was counted. By comparing the number of plaques with that of the non-treated group, plaque formation 50% inhibitory rate ($IC_{50}$) was determined.

The result was 1.6 µg/mL.

(2) The effect of T-1105 on foot-and-mouth disease virus (serotypes A, C, and Asia 1) was determined.

The viral concentrations for A, C, and Asia 1 were 10 $TCID_{50}$, 10 $TCID_{50}$, and $10^{1.5}$ $TCID_{50}$, respectively. After the virus was adsorbed onto IBRS-2 cells at 37° C. for 1 hour, 20 µg/mL of T-1105 was diluted by 2 steps and each of diluted solution was added to the cells, and 48 hours later the cells were fixed and stained with 10% neutral buffered formalin containing 0.2% crystal violet. When inhibition of the cytopathic effect was observed in one or more wells out of 4 wells at each concentration, the concentration was determined as effective. The result is shown in Table 1.

TABLE 1

| Foot-and-mouth disease virus serotypes | 25% or more inhibitory concentration (µg/mL) |
|---|---|
| Asia 1 | 0.625 |
| A | 0.313 |
| C | 1.25 |

T-1105 exhibited an excellent effect on the foot-and-mouth disease virus.

Test Example 2(1)

Pharmacokinetic Study of T-1105 (Pigs, Bovine)

1% T-1105 compounded feed was administered orally to pigs (conventional, 10 kg of body weight, 2 individuals) and bovine (black-haired Japanese cattle, 200 kg of body weight, 2 individuals) at the dosage of 100 mg/kg. At 2 and 8 hours after the administration, 1.5 mL of blood was taken from the jugular vein in each animal using a heparin-rinsed syringe, centrifuged at 4° C. and 2000 rpm for 10 minutes, and 250 µL of the blood plasma was dispensed into a 1.5 mL microtube. Based on a calibration curve prepared using blank plasma, the concentration of T-1105 was measured. To prepare a calibration curve, the same procedure was conducted as pretreatment for the plasma by adding 50 µL of 5 times concentrated T-1105 solution to 200 µL of blank plasma. To each of 250 µL of plasma test sample and plasma test sample for a calibration curve, 500 µL of methanol was added, and each of the resultant was stirred and centrifuged at 4° C. and 10000 rpm for 10 minutes. The supernatant was collected, deproteinized, and then evaporated to dryness. The residue was dissolved in 500 µL of the HPLC mobile phase, the resultant solution was centrifuged at 10° C. and 3000 rpm for 10 minutes, and the supernatant was collected for measurement. The HPLC measurement conditions were as follows.
Analytical column: Develosil ODS-MG-5 (4.6 mm I.D.×250 mm), Nomura Chemical Co., Ltd.
Guard column: Develosil ODS-MG-5 (4.0 mm I.D.×10 mm), Nomura Chemical Co., Ltd.

Column temperature: 40° C.
HPLC mobile phase: methanol/1 mol/L phosphate buffer (pH 7.0)/distilled water/TBA-Br (50:50:900:1.6, v/v/v/w)
Flow rate: 1.0 mL/min
Detection wavelength: 350 nm
Injection volume: 100 μL
Autosampler temperature: 10° C. preset
Analysis time: approximately 18 min The calibration curve was prepared, and the concentrations of T-1105 in plasma test samples for the respective individuals were determined based on the peak area and averaged.

Test Example 2(2)

Pharmacokinetic Study of T-1105 (Sheep)

1% T-1105 compounded feed was administered orally to sheep (Corriedale, 63 kg and 67 kg of body weight, 2 individuals) at a dosage of 100 mg/kg. At 2 and 8 hours after the administration, 1.5 mL of blood was taken from the jugular vein in each animal using a heparin-rinsed syringe, centrifuged quickly at 4° C. and 2000 rpm for 10 minutes, and 250 μL of the blood plasma was dispensed into a 1.5 mL microtube. 500 μL of methanol was added to plasma test sample, which was stirred and centrifuged at 4° C. and 10000 rpm for 10 minutes. The supernatant was collected, deproteinized, and evaporated to dryness. The residue was dissolved in 500 μL of the HPLC mobile phase, the resultant solution was centrifuged at 10° C. and 3000 rpm for 10 minutes, and the supernatant was collected for measurement. The measurement was conducted under the same condition as the Test Example 2(1).

A calibration curve was prepared with the standard solution and the concentrations of T-1105 in plasma test samples for the respective individuals were determined based on the peak area and averaged.

The result of the Test Example 2(1) and (2) is shown in Table 2.

TABLE 2

| | Plasma concentration (μg/mL) | |
|---|---|---|
| | 2 hrs after administration | 8 hrs after administration |
| Pigs | 75.0 | 36.4 |
| Sheep | 30.9 | 10.2 |
| Cattle | 7.86 | 0.173 |

T-1105 retained a high blood concentration in pigs and sheep, exhibiting excellent pharmacokinetics.

Test Example 3

Efficacy Test of Mixed-Feed Administration

The therapeutic effect of T-1105 on foot-and-mouth disease was evaluated using a pig systemic infection model.

Pigs (conventional, 10 kg of body weight, 2 individuals in administered group (No. 1 and 2), and 2 in non-administered group (No. 3 and 4)) were inoculated with $10^6$ TCID$_{50}$ of the foot-and-mouth disease virus in their forefoot pad and initiated infection.

T-1105 was orally administered as mixed feed at 200 mg/kg 1 hour before virus inoculation, then twice a day (400 mg/kg/day) for 6.5 days. The course of clinical sign was observed up to 8 days after the virus inoculation. Also, the course of viral load in the plasma and the nasal swab was determined up to 3 days after virus inoculation.

The course of clinical sign is shown in Table 3, the plasma viral load in Table 4, and the viral load in the nasal swab in Table 5 below.

TABLE 3

| | | Days after virus inoculation | | | | | | | | |
|---|---|---|---|---|---|---|---|---|---|---|
| | Pig No. | 0 | 1 | 2 | 3 | 4 | 5 | 6 | 7 | 8 |
| T-1105 administered group | 1 | − | − | − | − | − | − | − | − | − |
| | 2 | − | − | − | − | − | − | − | − | − |
| T-1105 non-administered group | 3 | − | − | + | ++ | ++ | ++ | ++ | ++ | ++ |
| | 4 | − | − | − | + | + | ++ | ++ | ++ | ++ |

−: normal,
+: lameness,
++: astasia

The T-1105 non-administered group animals showed lameness, dysstasia, and blister formation in their feet on and after the day 2 of virus inoculation, while the T-1105 administered group animals exhibited no change in their appearance.

TABLE 4

| | | Days after virus inoculation | |
|---|---|---|---|
| | Pig No. | 1 | 3 |
| T-1105 administered group | 1 | <0.14 | <0.14 |
| | 2 | <0.14 | <0.14 |
| T-1105 non-administered group | 3 | <0.14 | 34891 |
| | 4 | 0.18 | 282.7 |

Unit: TCID$_{50}$/μL

The plasma viral load increased sharply in the T-1105 non-administered group, while it remained at the detection limit or bellow in the T-1105 administered group.

T-1105 exhibited an excellent therapeutic effect in the pig systemic infection model.

TABLE 5

| | | Days after virus inoculation | |
|---|---|---|---|
| | Pig No. | 1 | 3 |
| T-1105 administered group | 1 | <0.07 | <0.07 |
| | 2 | <0.07 | <0.07 |
| T-1105 non-administered group | 3 | <0.07 | 160 |
| | 4 | <0.07 | 0.66 |

Unit: TCID$_{50}$/μL of swab solution

The viral load in the nasal swab increased in the T-1105 non-administered group, while it scarcely increased in the T-1105 administered group.

T-1105 exhibited an excellent therapeutic effect in the pig systemic infection model.

Furthermore, the pigs in the T-1105 administered group exhibited no toxic finding during the administration period.

Test Example 4

Cytotoxicity

In a 96-well plate (IWAKI Co., Ltd.), a culture medium containing a predetermined concentration of T-1105 was loaded at 100 μL/well. Then, Vero cells were prepared at $2\times10^4$ cells/mL with the culture medium, the resultant was seeded at 100 μL/well and cultured under the condition of 5% $CO_2$ at 37° C. for 4 days. At the end of cultivation, the number of viable cells was determined by the XTT method (for example, CANCER RESEARCH, vol. 48, pp. 4827-4833 (1988)).

The 50% cell growth inhibitory concentration ($IC_{50}$) of T-1105 was 250 μg/mL or more.

As is evident from the result above, T-1105 is quite safe, and effective as an anti-foot-and-mouth disease virus agent for Suidae animal, etc., in treating foot-and-mouth disease induced by the foot-and-mouth disease virus.

Formulation Example 1

Tablets 10 g of T-1105 was mixed with 4.4 g of lactose, 4.4 g of crystalline cellulose, 1.0 g of sodium carboxymethyl starch and 0.20 g of magnesium stearate, and then the powder mixture was compressed into a tablet of 200 mg to give a tablet which contains 100 mg of T-1105 per tablet.

Formulation Example 2

Compounded Feed 30 g of T-1105 was mixed with 2970 g of commercially available feeds for pigs (JA ZEN-NOH) to obtain 3000 g of 1% T-1105 compounded feed. In this feed, T-1105 had been stable without being degraded for 24 hours.

INDUSTRIAL APPLICABILITY

The anti-foot-and-mouth disease agent containing T-1105 or a salt thereof is useful for the treatment including prevention or therapy of foot-and-mouth disease for the Suidae animals, etc.

The invention claimed is:

1. A method for treating a disease caused by a foot-and-mouth disease virus comprising administering to a pig in need thereof an effective amount of 3-oxo-3,4-dihydro-2-pyrazinecarboxamide or a salt thereof.

2. A method for treating a disease caused by a foot-and-mouth disease virus comprising administering to a sheep in need thereof an effective amount of 3-oxo-3,4-dihydro-2-pyrazinecarboxamide or a salt thereof.

3. The method of claim 1, wherein 3-oxo-3,4-dihydro-2-pyrazinecarboxamide or a salt thereof is administered orally.

4. The method of claim 2, wherein 3-oxo-3,4-dihydro-2-pyrazinecarboxamide or a salt thereof is administered orally.

5. The method of claim 1, wherein 3-oxo-3,4-dihydro-2-pyrazinecarboxamide or a salt thereof is administered in a therapeutic composition formulated for a pig.

6. The method of claim 2, wherein 3-oxo-3,4-dihydro-2-pyrazinecarboxamide or a salt thereof is administered in a therapeutic composition formulated for a sheep.

7. The method of claim 1, wherein 3-oxo-3,4-dihydro-2-pyrazinecarboxamide or a salt thereof is administered in a pig feed.

8. The method of claim 2, wherein 3-oxo-3,4-dihydro-2-pyrazinecarboxamide or a salt thereof is administered in a sheep feed.

9. The method of claim 1, wherein 3-oxo-3,4-dihydro-2-pyrazinecarboxamide or a salt thereof is administered by injection.

10. The method of claim 2, wherein 3-oxo-3,4-dihydro-2-pyrazinecarboxamide or a salt thereof is administered by injection.

11. The method of claim 1, wherein 3-oxo-3,4-dihydro-2-pyrazinecarboxamide or a salt thereof is administered in an amount of 1 to 2,000 mg/kg of body weight per day.

12. The method of claim 2, wherein 3-oxo-3,4-dihydro-2-pyrazinecarboxamide or a salt thereof is administered in an amount of 1 to 2,000 mg/kg of body weight per day.

13. The method of claim 1, wherein said disease is caused by foot-and-mouth disease virus European serotype A, O or C; Asian serotype Asia 1; or African serotype SAT1, SAT2 or SAT3; or subtypes thereof.

14. The method of claim 2, wherein said disease is caused by foot-and-mouth disease virus European serotype A, O or C; Asian serotype Asia 1; or African serotype SAT1, SAT2 or SAT3; or subtypes thereof.

* * * * *